Figure 1:
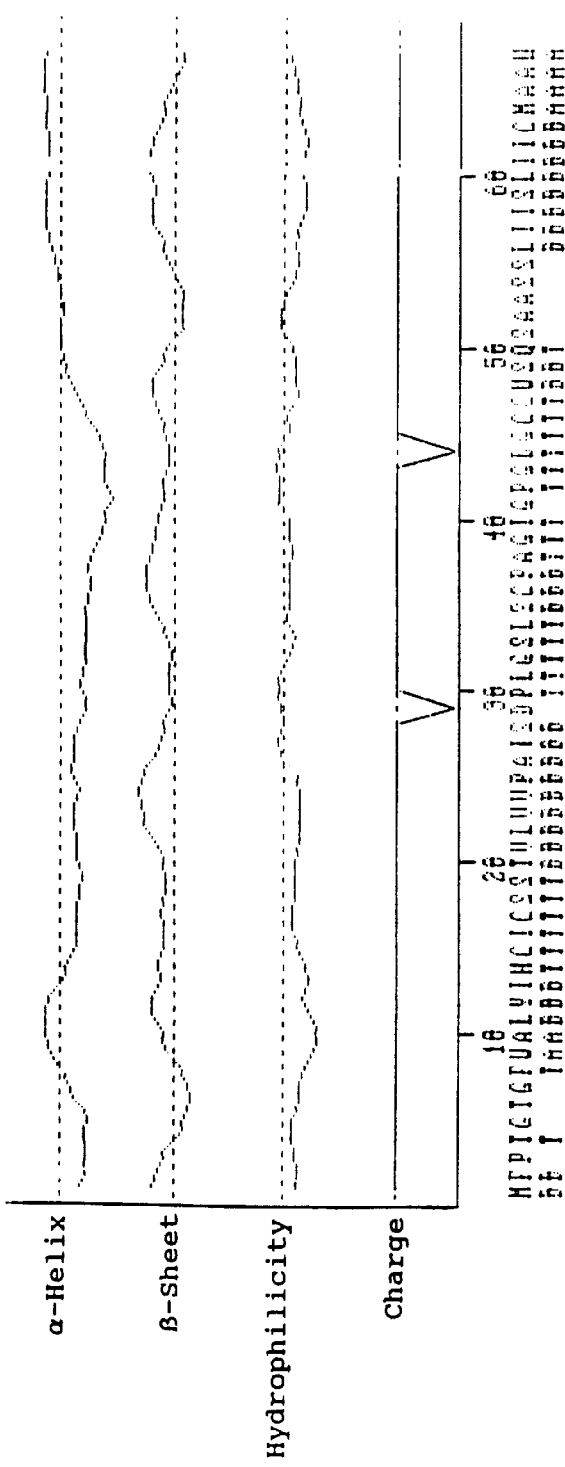

United States Patent [19]
Dietrich et al.

[11] Patent Number: 5,861,243
[45] Date of Patent: Jan. 19, 1999

[54] VACCINE FOR PROTECTION AGAINST HIV INFECTIONS, PROCESS FOR PREPARING SAME AND THEIR USE AS DIAGNOSTIC AND AGENT IMMUNOTHERAPEUTIC AGENT

[75] Inventors: Ursula Dietrich, Eschborn; Michalina Adamski, Frankfurt; Hagen Von Briesen, Kronberg; Herbert Kühnel, Egelsbach; Helga Rübsamen-Waigmann, Bad Soden, all of Germany

[73] Assignee: Chemotherapeutisches Forschunginstitut Georg Speyer-Haus Zu Frankfurt A.M., Frankfurt a.M., Germany

[21] Appl. No.: 968,689

[22] Filed: Nov. 12, 1997

Related U.S. Application Data

[63] Continuation of Ser. No. 780,132, Dec. 26, 1996, abandoned, which is a continuation of Ser. No. 205,761, Mar. 4, 1994, abandoned, which is a continuation of Ser. No. 868,351, filed as PCT/EP90/01729 Oct. 12, 1990 published as WO91/05567 May 2, 1991, abandoned.

[30] Foreign Application Priority Data

Oct. 14, 1989 [DE] Germany .......................... 39 34 366.9

[51] Int. Cl.$^6$ ....................................................... C12Q 1/70
[52] U.S. Cl. ..................... 435/5; 435/6; 435/7.1; 435/974; 530/327; 530/328; 530/329; 424/186.1; 424/188.1
[58] Field of Search ............................ 435/5, 6, 7.1, 974; 530/327, 328, 329; 424/186.1, 188.1

[56] References Cited

FOREIGN PATENT DOCUMENTS

| | | |
|---|---|---|
| 0283327 | 9/1988 | European Pat. Off. . |
| 0347365 | 12/1989 | European Pat. Off. .......... C12N 7/00 |
| 8805440 | 7/1988 | WIPO .............................. C07K 7/10 |

OTHER PUBLICATIONS

Norley, S. et al. 1992. Immunobiol. vol. 184 pp. 193–207.
Kühnel, et al, 1989, "Molecular cloning of two West African . . . " PNAS 86: 2383–2387.
Greene, "AIDS and the Immune System" Scientific American, Sep., 1993, pp. 99–105.
Brown, "AIDS Vaccine Trials Viewed With Caution" Washington Post Newspaper, Jun. 10, 1993.
J.F. Zagury et al., "Genetic variability between isolates of human immunodeficiency virus (HIV) . . . " Proc. Natl. Acad. Sci. USA, vol. 85, pp. 5941–5945, Aug. 1988, pp. 5941–5945.
V.M. Hirsch et al., "An African primate lentivirus (SIVsm) closely related to HIV–2", Nature, vol. 339, Jun. 1, 1989, pp. 389–391.

*Primary Examiner*—Jeffrey Stucker
*Attorney, Agent, or Firm*—Jacobson, Price, Holman & Stern, PLLC

[57] ABSTRACT

Vaccine for protection against HIV infections, therapeutic agents for treatment subsequent to HIV infections, process for their preparation and their use; procedure for differentiation between HIV-$2_{ALT}$ type infections and HIV-2 infections defined by the prototype HIV-$2_{ROD}$.

Subject matter of the present invention are the virus HIV-$2_{D205}$ as well as HIV-2 variants distinguishing from the HIV-2 prototypes of the type HIV-$2_{ROD}$ in that nucleotide sequence homology is less than 77%. Further, proteins and nucleic acids of HIV-$2_{D205}$ and its variants for utilization as vaccines for protection against HIV infections, for geno- or immunotherapy, for establishing an animal model, and for differential diagnostics are part of this invention. Furthermore, the processes for preparing these vaccines, immunotherapeutic and diagnostic agents as well as their use are part of this invention.

19 Claims, 6 Drawing Sheets

FIG. 2

```
HIV-2_RCO     MM...NQLLIAILLASACLVYCTQYVTVFYGVPTWKNATIPLFCATRNRDTWGTIQCLPDNDDYQ  62
HIV-2_D205    -AYFSSR-P--L--IGISGFV-K---------I-A-R---V--I---T-------V------G--T  65
HIV-2_D194    -EPGR----V----T----I--K---------I-A-R--S-------K---------------    65
SIV_SM        -GCLG-------L--V-VLEIC-V----------A--------K-------T----------S    65
SIV_MAC251    -GCLG----------L-VYGI-----------A-R---------K-------T------G--S    65

HIV-2_RCO     EITLNVTEAFDAWNNTVTEQAIEDVWHLFETSIKPCVKLTPLCVAMKCSSTE....SSTGNNTTS  123
HIV-2_D205    --R--I-------D----Q--VN---R-----------------N--K--....TNP--..A-   124
HIV-2_D194    --------------D-------------R---------------N-NI-.....----..--.   122
SIV_SM        -LAI---------D------------N----------I--R-NK--TDRWGL---AG-T       130
SIV_MAC251    -LA----S----E----------E---------S---IT-R-NKS-TDRWGL-.....K-     126

HIV-2_RCO     KSTSTTTTTPTDQEQEIS.....EDTPCARADNCSGLGEEETINCQFNMTGLERDKKKQYNETWY  183
HIV-2_D205    ST-T-KP--TSRGLKT-N.....-ID--IKN-S-T------IMQ-N-S----R--EL---KD---  184
HIV-2_D194    ATP-PPNI-II-....W..........-IGDN--T---K--VVE-E------Q---RK--NA--  176
SIV_SM        TTAI---A--SVA-NV-N.....-SN--IKNNS-A--EQ-PN-G-K----H-----E------   190
SIV_MAC251    .---TI--AA--SAPVSEKIDMVN--TSS-IAQN--T--EQ-QM-S-K-T----K---T-E----- 185

HIV-2_RCO     SKDVVCETNNST.NQTQCYMNHCNTSVITESCDKHYWDAIRFRYCAPPGYALLRCNDTNYSGFAP  247
HIV-2_D205    -E-LE-...--TRKYTSR--IRT---TI-Q---------SL---------FF-----------M- 247
HIV-2_D194    -R----DKT-G-..G-.---R-----K---------MK--------F--------------E-   238
SIV_SM        -R-LI--QSANE.SESK---H-----Q-------------------------S--L----     254
SIV_MAC251    -T-L---QG---D-ESR-------Q-------T--------------------------M-    250

HIV-2_RCO     NCSKVVASTCTRMMETQTSTWFGFNGTRAENRTYIYWHGRDNRTIISLNKYYNLSHCKRPGNKI  312
HIV-2_D205    ---------S--------S------------EK--------T----I---------T       312
HIV-2_D194    K------AS----------------------K-------------TM--------T        303
SIV_SM        -------V-S---------------------KS-----------TMR-R--E--T         319
SIV_MAC251    K------V-S---------------------------------TMK-R----T           315

HIV-2_RCO     VKQIMLMSGHVFHSHYQPINKRPRQAWCWFKGKWKDAHQEVKETLAKHPRYRG..TNDTRNISFA  375
HIV-2_D205    -VP-RTV--LL---..----------------N-TE-IK---R-II----K-GAK-I-SVKLVS  375
HIV-2_D194    -VP-T----RR---.RPVY--K-G------Q-N-IE--R---Q--------G-...---GK-N-T 365
SIV_SM        -LPVTI---L----..----E--K------E-S--K-I-------V-----T-...----K-NLT 380
SIV_MAC251    -LPVTI---L----..--LTD--K------G------IK---Q-IV-----T-..-N-DK-NKT 376

HIV-2_RCO     APGKGSDPEVAYMWTNCRGEFLYCNMTWFLNWIENK................THRNYAPCHIKQII 425
HIV-2_D205    EH-----                                                            382
HIV-2_D194    K--I-------T--------------------V---TN........--G------R---      427
SIV_SM        --.A-G----TF-------------K-N-----V-DRDEKGGRWKQQNRKEQQKK--V----R--- 429
SIV_MAC251    ---.-G----TF-------------K-N-----V-DRDVTTQRPKQR.....HR---V----R--- 435

HIV-2_RCO     NTWHKVGRNVYLPPREGELSCNSTVTSIIANIDWQNNNQTNITFSAEVAELYKLELGDYKLVEIT 490
HIV-2_D205
HIV-2_D194    --------T------------T---------....SDG---------------------I-V-   491
SIV_SM        --------K---------D-T------L--E---I-S-E---N------------------I---  494
SIV_MAC251    --------K---------D-T------L----TDG---S--N------------------     500

HIV-2_RCO     PIGFAPTKEKRY.SSAHGRHTR  511
HIV-2_D205
HIV-2_D194    --P----------.---PV-NK-  512
SIV_SM        ---L---SVR--TTTGAS-NK-  515
SIV_MAC251    ---L---DV---TTGGTS-NK-  521
```

VACCINE FOR PROTECTION AGAINST HIV INFECTIONS, PROCESS FOR PREPARING SAME AND THEIR USE AS DIAGNOSTIC AND AGENT IMMUNOTHERAPEUTIC AGENT

This application is a continuation of application Ser. No. 08/780,132, filed Dec. 26, 1996, now abandoned, which is a continuation of application Ser. No. 08/205,761, filed Mar. 4, 1994, now abandoned, which is a continuation of application Serial No. 07/868,351, filed Apr 13, 1992, now abandoned, which is a 371 of PCT/EP90/01729, filed Oct. 12, 1990.

Subject matter of the invention are vaccines for protection against HIV infections, a process for their preparation and their use.

Previous antiviral medicaments to which effectiveness against HIV has also been attributed, have the disadvantage of possessing a mostly poor antiviral spectrum associated with relatively high toxicity. Many of these substances affect a viral thymidine kinase or a viral polymerase. With these substances, however, development of resistance of the infecting viruses has been observed even during therapy.

A group of substances for which activity against HIV has been established includes Foscarnet (phosphono formate). This substance acts as an inhibitor of viral reverse transcriptase but is, due to its toxicity determined in clinical tests, not suitable for prophylaxis or therapy of retrovirus infections [B. Öberg, "Antiviral Effects of Phosphono Formate (PFA, Foscarnet Sodium)", Pharm.Ther. 19 (1983), p. 387–415].

Another inhibitor of reverse transcriptase is the substance Suramin. However, due to its toxicity for the mammal organism, it is likewise not suitable for prophylaxis or therapy of HIV infections [H. Mitsuya et al., "Suramin Protection of T-Cells in vitro against Infectivity and Cytopathic Effect of HTLV-III", Science 226 (1984), p. 172–174].

Further development then resulted in inhibitors of reverse transcriptase being less toxic for the mammal organism including substances such as dextran sulfate and pentosan polysulfate which demonstrably have an inhibiting effect to HIV I in vivo. This is described in the laid-open documents DE 3,601,136 and EP 0,293,826.

Therefore, previous efforts to develop agents for the prophylaxis and therapy of HIV infections focused on the inhibition of HIV I reverse transcriptase.

In principle, besides chemotherapeutic treatment of HIV infections, there is the possibility of geno- or immunotherapy. Gene therapy comprises invasion of viral nucleic acid parts into human cells, especially into the target cells of HIV, the CD4-positive cells of the immune system, for instance. By forming an "antisense" RNA, i.e., an RNA complementary to the messenger RNA (mRNA), the viral mRNA can be neutralized and hence, further virus growth inhibited. In another embodiment, oligonucleotides or structures chemically related thereto, which are complementary to the mRNA, may be employed. In immunotherapy, following infection, antigens are administered which are expected to support immune response to HIV.

However, in order to prevent further spreading of the AIDS epidemic it would be urgingly necessary to develop a vaccine for protection against HIV infections. Here, the main problem is the high variability of HIV: protective vaccination should and must include all possible virus variants. One way to that is, by comparing HIV virus variants in maximum possible number and of evolutionary great difference, to detect conserved areas in the viral antigens which then, as peptides are capable to induce formation of protective antibodies in humans. Alternatively, the peptides may be employed in another organism to form antibodies, so that the antibodies are given to humans directly for protection. In addition to conserved peptides, an effective vaccine must also include such peptides which derive from strongly divergent strains.

Two types of viruses, HIV-1 and HIV-2, could be isolated from patients having the immune deficiency disease AIDS (Barré-Sinoussi et al., Science 220, 868–871; Clavel et al., Science 233, 343–346). Both are retroviruses of the subfamily Lentivirus having tropism for CD4-positive cells. HIV-2 differs from HIV-1 in several respects: firstly, the antigens differ in size and their epitopes. This is the reason why HIV-2 are recognized only very poorly by serological assays for HIV-1. Secondly, the genetic structure of HIV-2 is somewhat different, as HIV-1 has the gene vpu, and HIV-2 has the gene vpx. Thirdly, both types of viruses differ in their nucleotide sequences; homology between HIV-1 and HIV-2 is only 55–60% while homology between independently isolated HIV-1 strains is 87–94%, and is 87–90% between different HIV-2 strains. Fourthly, the major spreading area of both types of viruses in Africa is different: HIV-1 is endemic in Central Africa while HIV-2 mainly occurs in Western Africa.

HIV-1 and HIV-2 are more closely related to certain immune deficiency viruses of monkeys (SIV) than to each other. The closest relative of HIV-1 is the chimpanzee virus $SIV_{CPZ}$ (Huet et al., Nature 345, 356–359, 1990) having about 75% homology, while viruses from macaques, $SIV_{mac}$ (Franchini et al., Nature 328, 539–543, 1987), and from mangabeys, $SIV_{sm}$ (Hirsch et al., Nature 339, 389–392), each having about 75% homology, are the most similar ones to HIV-2. HIV-2, $SIV_{mac}$ and $SIV_{sm}$ are of the same serotype and hence, are to be regarded as different sub-types of a major virus group.

In the older, but not previously published EP 89,710, 057.4, there is described a HIV-2 virus variant, namely $HIV-2_{D205}$ (also termed $HIV_{ALT}$, which can be cloned from the corresponding virus isolate $HIV-2_{D205}$. The virus isolate $HIV-^{2}D_{205}$ has been deposited according to the Budapest Treaty on Dec. 23, 1987, under the number ECACC V 87,122,304 at the European Collection of animal Cell Cultures (ECACC), Porton Down, Salisbury, Wiltshire, Great Britain, SP40JG. Also described are RNAs and DNAs derived therefrom as well as the proteins of the virus isolates.

The virus $HIV-2_{D205}$ defines an alternative subtype of the $HIV-2/SIV_{mac}/SIV_{sm}$ virus group. This virus is derived from an asymptomatic HIV-positive Ghanaian woman. $HIV-2_{D205}$ reacted strongly in the HIV-2 assay, but many viral antigens were of different size. However, determination of the nucleotide sequence revealed that $HIV-2_{D205}$ is a highly divergent strain. Homology between $HIV-2_{D205}$ and the previously sequenced HIV-2 strains (ROD: Guyader et al., Nature 326, 662–669, 1987; NIHZ: Zagury et al., PNAS 85, 5941–5945, 1988; ISY: Franchini et al., PNAS 86, 2433–2437, 1989; D194: Kuhnel et al., PNAS 86, 2383–2387, 1989) is only about 76%. Thus, $HIV-2_{D205}$ genetically falls exactly between these HIV-2 strains (herein termed as ROD type) and the monkey viruses $SIV_{mac}/SIV_{sm}$ (each having about 75% homology). Phylogenetic tree analyses revealed that the origin of $HIV-2_{D205}$ must be situated well before separation between the HIV-2 ROD type viruses and the monkey viruses $SIV_{mac}/SIV_{sm}$. Hence, $HIV-2_{D205}$ evolutionarily stands very close to a common ancestor of the total virus group $HIV-2/SIV_{mac}/SIV_{sm}$.

In the development of vaccines, therapeutic or diagnostic agents, it is absolutely necessary to consider viruses such as HIV-2$_{D205}$. Vaccines must offer protection against all variants of an infectious pathogen. Where vaccines are derived from constant regions of a phylogenetically old virus, it is to be expected that they cover a very broad spectrum of variants. The same is true for peptides, antibodies, nucleic acids or other substances derived from the nucleotide sequences, which are employed as genetic or immunotherapeutic agents against HIV. Diagnostic agents intended to distinguish betweeen ROD type and D205 type viruses must, however, be derived from those sequential areas which result in antigens differing as much as possible.

In addition, a virus such as HIV-2$_{D205}$ standing phylogenetically between HIV-2 and the monkey viruses SIV$_{mac}$/SIV$_{sm}$ presents itself for establishing a monkey model for AIDS. HIV-2$_{D205}$ is the immune deficiency virus isolated from humans which is by far the most similar to this monkey virus, and therefore, it could behave in monkeys like a monkey virus and possibly induce disease as well.

In the development to date of a vaccine against HIV infection, the difficulty arises that at present, no suitable animal model for this disease exists. This is the reason why development of inoculation strategies, for example, against the property of the virus to modify the composition of its protein coat and to incorporate its own genes into the host's genetic material, is making but slow progress. Furthermore, the vaccine must guarantee sufficient protection against the complete spectrum of the numerous HIV variants found hitherto. Likewise, however, the vaccine itself must not involve the risk of HIV infection.

Now, in further sequencing HIV-2$_{D205}$ and phylogenetic tree ana-lyses carried out subsequently, it surprisingly was found that HIV-2$_{D205}$ is genetically equidistant to the previously described HIV-2 strains as well as to the monkey viruses SIV$_{mac}$ and SIV$_{sm}$. Thus, HIV-2$_{D205}$ is a common precursor of the HIV-2/SIV$_{mac}$/SIV$_{sm}$-group and is evolutionarily very close to same and, hence, is a very old virus.

Therefore, this virus presents itself as a starting material for the production of a vaccine, a genetic or immunotherapeutic agent with broad spectrum of protection against the viruses of this group. At the same time, due to its close relationship to the monkey viruses, HIV-2$_{D205}$ might be particularly suitable for establishing an animal model. To establish an animal model, HIV-2$_{D205}$is transferred to suitable primates (e.g., rhesus monkeys), and establishment of infection and, optionally, occurring symptoms are monitored. At the same time, establishing an animal model using HIV-2$_{D05}$ as the virus permits one to test the prepared vaccines, genotherapeutic or immunotherapeutic agents.

Therefore, it is object of the present invention to provide a vaccine for the protection against HIV infections which has an activity spectrum against various types of the group HIV-2/SIV as broad as possible, and which permits establishment of an animal model necessary for the development of the vaccine.

This problem is solved by preparing the vaccines from the virus HIV-2$_{D205}$.

A preferred embodiment is a vaccine suitable for therapeutic utilization prior to infection. It is another preferred embodiment that the vaccine as an immunotherapeutic agent is suitable for utilization subsequent to infection and likewise covers a broad spectrum of variants.

In a further embodiment, the vaccine consists of the peptides

1. LFETSIKPCVKL 2. ESCDKHYWD
3. RFRYCAPPG 4. LLRCNDTNYSGF
5. STWFGFNGTRAENRYIYWH 6. DNRTIISLN
7. NELDRFGLAESLLE 8. PLVPTGSENLKSL
9. PLSPRTLNAWVKL
10. EEKKFGAEVVPGFQALSEGCTPYEINQMLNCV
11. GLQKCVRMYNPTNILD 12. FQSYVDRFYKSLRAEQTD
13. QNANPDCKLVLKGL 14. NPTLEEMLTACQG
15. GGPGQKARLMAEALKE 16. ARQCRAPRRQGCWKCGK or combinations thereof.

Furthermore, subject matter of the invention is a process for preparing a vaccine for protection against HIV infections from the virus HIV-2$_{D205}$ and use of the virus HIV-2$_{D205}$ for the preparation of a vaccine.

In another embodiment, the virus is transferred into a suitable animal host and grown therein. Then, the formed antibodies, subsequent to appropriate work-up as known in prior art for other vaccines as well, are used as passive vaccine against HIV infection. As the animal hosts, in particular, suitable monkey species may be used, but also animals capable of being immunized without falling ill (e.g., rabbits) (Filice et al., Nature 335, 366–369, 1988).

Likewise, human monoclonal antibodies against HIV-2$_{D205}$ present themselves as a possible mechanism of protection.

In a further embodiment, DNA of which an RNA complementary to the viral mRNA can be transcribed completely or partially, in a suitable vector, is transfected into human immune system cells and thus introduced into the human. Hence, viral mRNA is competitively excluded from the further growth cycle. Likewise, synthetic oligonucleotides may be used for neutralizing viral mRNA.

For differential diagnostics, selected areas of HIV-2$_{D205}$ DNA are used which either do not occur at all in the prototype HIV-2$_{ROD}$ or deviate considerably (more than 30%). Using common techniques (marking with radio-active isotopes, immunofluorescence test, ELISA, etc.), peptides or nucleic acids are prepared. A region being unique for HIV-2$_{D205}$ is, e.g., a 54 base pairs (bp) insertion in the overlap region of the two open reading frames gag and pol having the sequence AACCCAGCAGAGGGCATGACACCTCGGGGGGCGACACCATCTGCGCCCCCTGCA. (SEQ ID No. 17)

Other highly variable regions besides the coat protein env are the genes rev and vif.

Previous examinations of HIV-2D$_{205}$, an isolate of an asymptomatic Ghanaian woman, showed growth of lymphocytes without cytopathic effects and good growth on macrophages [Kuhnel, H., et al., Proc.Natl.Acad.Sci. U.S.A. 86, p. 2383–2387 (1989)].

In the further examination of the virus HIV-2D$_{205}$ it was found that the clone contained 7817 base pairs (bp) of a proviral genome, setting out from the long terminal repeat (LTR). The clone possesses the following viral genes completely: "gag" for the virus core protein, "po0" for integration and replication (protease, reverse transcriptase, integrase), the infectivity factor "vif", the gene "vpx" typical for HIV-2 and the monkey viruses SIV$_{mac}$ and SIV$_{sm}$, the gene "vpr" which is responsible for rapid growth, and the two first exons of the positive regulator genes "tat" and "rev". The region encoding the external coat protein is contained in the clone with 4/5, the sequence of the negatively regulating factor "nef" with a half insofar as the latter overlaps with the right LTR, and left and right LTR are identical.

The sequence was compared to the previously known HIV and SIV sequences (cf. table 1). Surprisingly, it was found that nucleotide homology of the entire clone HIV-$2_{D205}$ to the previously known HIV-2 sequences is only 76.2–76.8%, whereas homology of the other HIV-2 sequences to each other is by far greater, being 87.0–89.3%. Homology to $SIV_{sm}$ and $SIV_{mac}$ is 76.4 and 75.0%, respectively, i.e., HIV-$2_{D205}$ equally differs from these two monkey virus sequences as from HIV-2. Homology to $SIV_{AGM}$ and HIV-1 is in the same range as for the other HIV-2 isolates.

Sequential comparisons of single genetic sections of HIV-$2_{D205}$, HIV-$2_{ROD}$, $SIV_{mac}$ and $SIV_{mac}$, showed that variability in the nucleotide region ranges from 4.6% (for R) up to 35.9% (for rev exon 1), and in the amino acid region from 12.8% (for gag) up to 47.6% (for rev exon 1) (cf. table 2).

In spite of such variability, functionally relevant sequences or protein characteristics such as hydrophilicity or charge were preserved to a high degree.

While the sequenced part of the external glycoprotein (gp) of HIV-$2_{D205}$ differed by 33% from that of HIV-$2_{ROD}$, it had the same pattern of conserved and variable regions as the other HIV-2 and $SIV_{sm}/SIV_{mac}$ sequences (see FIG. 2). All the cysteine residues found in the external glycoproteins of HIV-$2_{ROD}$ were preserved. Deviations in the external glycoproteins are due to single amino acid exchange and to minor deletions or insertions mostly in the variable regions. Additionally, a large number of modified glycosylation sites were observed. The external gp of HIV-$2_{D205}$ contains only 13 out of 21 potential N-glycosylation sites of the corresponding HIV-$2_{ROD}$ gp, emphasizing the importance of glycosylation in the production of envelope variability.

By immunoprecipitation of viral proteins from infected cells and subsequent analysis using SDS poly-acrylamide gel electrophoresis, it was found that the external coat proteins of HIV-$2_{D205}$ have higher molecular weights than those of the type HIV-$2_{ROD}$.

Figure 3:
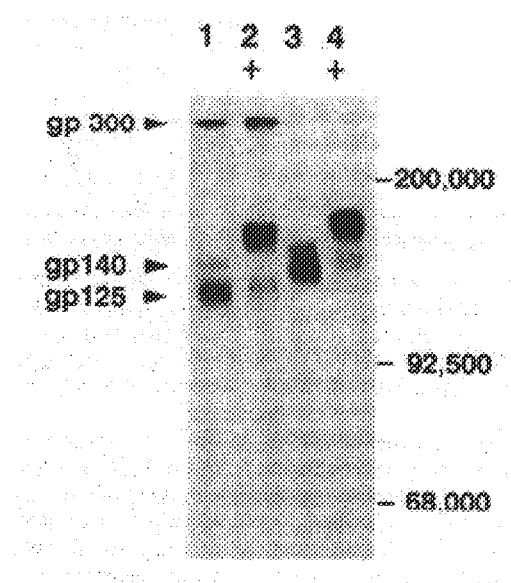

In contrast to the other HIV-2 and $SIV_{max}/SIV_{sm}$ strains, the coat protein precursor with HIV-$2_{D205}$ does not form a dimer (see FIG. 3).

Figure 4:
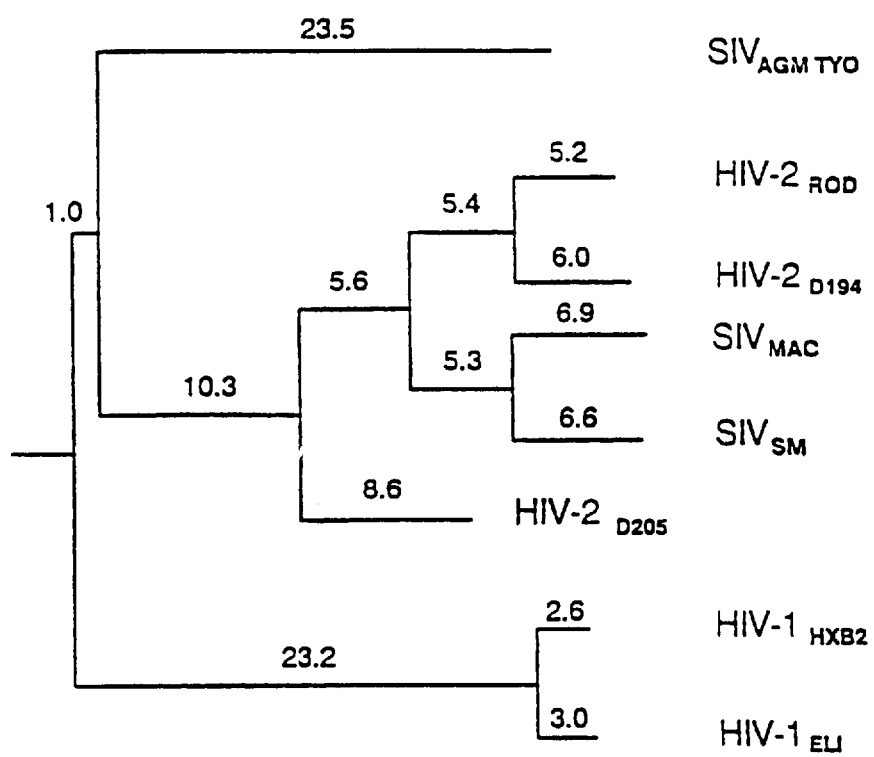

Thus, dimer formation said to be necessary for proper processing of the coat protein precursors of this virus group—in contrast to the viruses HIV-1—either is a relatively new development within the HIV-2/$SIV_{mac}SIV_{sm}$ group, or HIV-$2_{D205}$ represents an independent type of virus. In favor of this latter point is the classification of HIV-$2_{D205}$ within the phylogenetic tree of the viruses HIV/SIV (FIG. 4). This tree is based on the nucleotide variation in the 3'-part of HIV-$2_{D205}$. One can recognize therein that HIV-$2_{D205}$ differs by 24.8% from the HIV-2 prototype HIV-$2_{ROD}$, and by 26.1% and 26.4% from $SIV_{sm}$ and $SIV_{mac}$, respectively. This phylogenetic difference is well in accordance with the deviations in the nucleotide sequence determined directly by sequence comparisons (table 1). According to the phylogenetic tree analysis, the virus HIV-$2_{D205}$ is assigned to a common precursor of the types HIV-2/$SIV_{sm}/SIV_{mac}$ with a divergence of 8.6%. Therefore, the term HIV-$2_{ALT}$ is proposed for HIV-$2_{D205}$.

It is known to the artisan that pathogenity of a virus decreases with increasing host adaptation time. Thus, the virus $SIV_{sm}$ from sooty mangabey, for example, is not pathogenic for this monkey species, but if it is incorporated into another monkey species, e.g., into macaques, then it will turn pathogenic for this species. HIV-$2_{D205}$ is derived from an asymptomatic person, does not have cytopathic effect on lymphocytes, and is a relatively old virus. Hence, this virus could be a non-pathogenic HIV-2 group subtype. Therefore, it is also part of the invention to use HIV-$2_{D205}$ or antigens, peptides or nucleic acids thereof for differential diagnostics to distinguish between infections of the type HIV-$2_{D205}$ and those of the prototype HIV-$2_{ROD}$. Therefore, the virus HIV-$2_{D205}$ is also suitable for the preparation of genotherapeutic, immunotherapeutic and diagnostic agents.

Figure 5A:
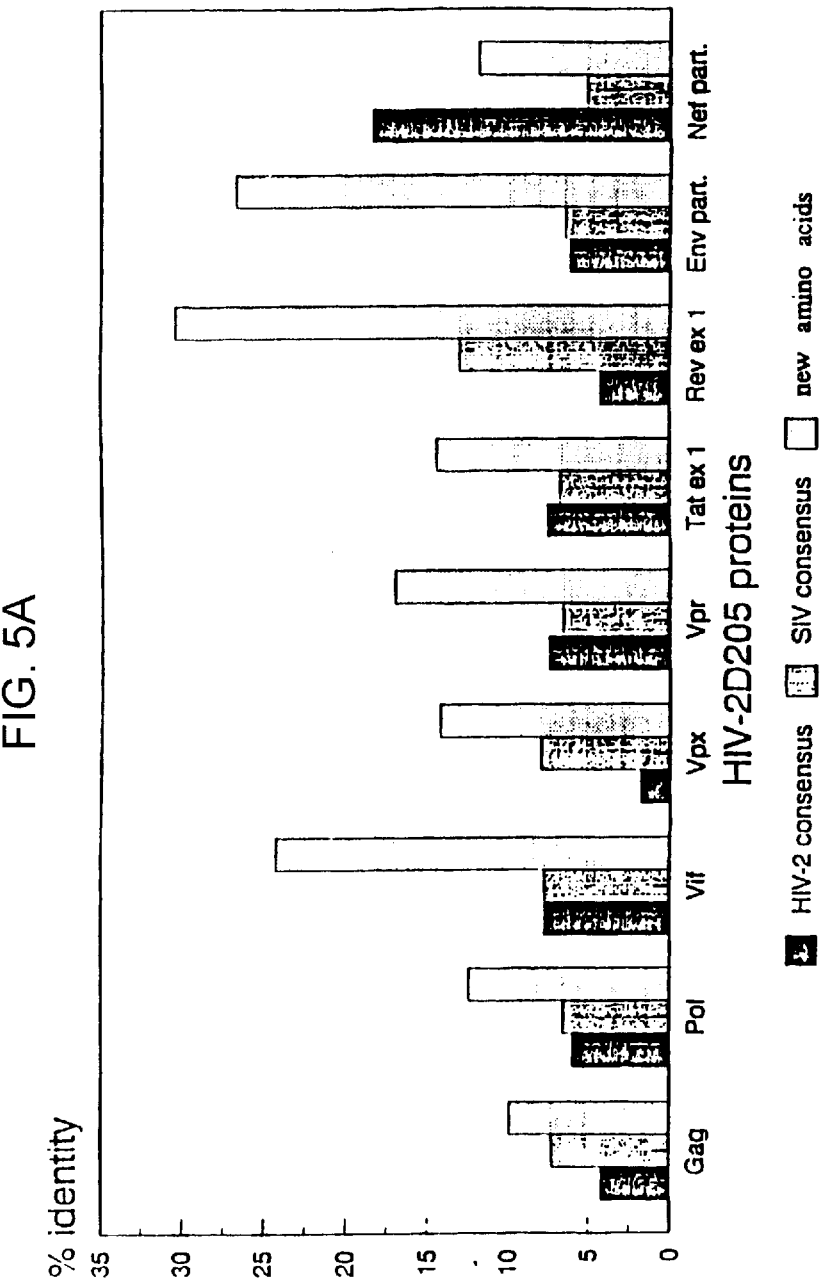
Figure 5B:
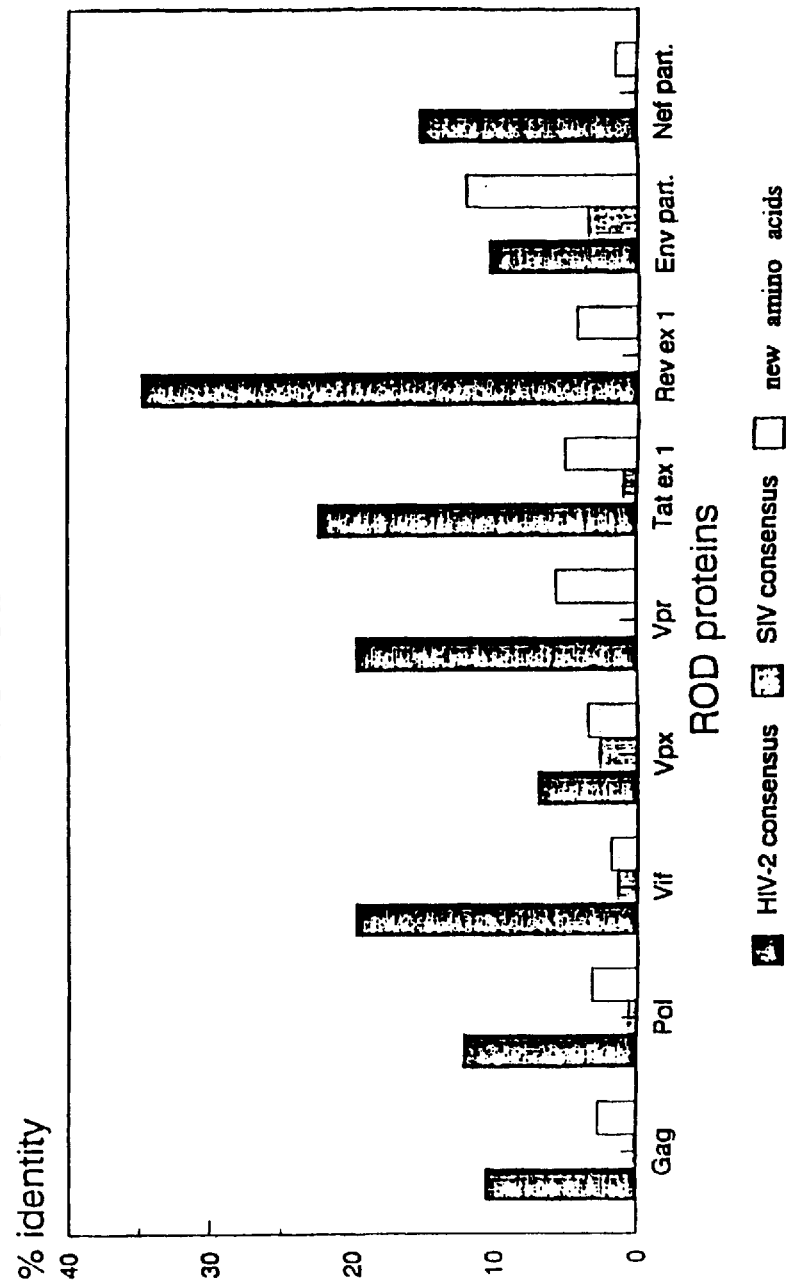

By comparing amino acid sequences of HIV-$2_{D205}$ proteins with the amino acid consensus sequences derived for the single genes from all the previously published HIV-2 and $SIV_{mac}/SIV_{sm}$, 6 conserved regions having at least 9 100% conserved amino acids result for the env region present, and 11 regions having at least 13 100% conserved amino acids for gag (FIG. 5). Peptides from this region preferably present themselves as a vaccine having broad activity spectrum, particularly, where said vaccine furthermore consists of a combination of theses peptides, with the peptides being the following:

1. LFETSIKPCVKL (SEQ ID NO. 1) 2. ESCDKHYWD (SEQ ID NO: 2)
3. (SEQ ID NO: 8) RFRYCAPPG 4. LLRCNDTNYSGF (SEQ ID. NO. 4)
5. STWFGFNGTRAENRYIYWH (SEQ ID NO: 5) 6. DNRTIISLN (SEQ ID NO:6)
7. NELDRFGLAESLLE (SEQ ID NO:7) 8. PLVPTG-SENLKSL (SEQ ID NO: 8)
9. PLSPRTLNAWVKL (SEQ ID NO:9)
10. EEKKFGAEVVPGFQALSEGCTPYEINQMLNCV (SEQ ID NO: 10)
11. GLQKCVRMYNPTNILD (SEQ ID NO:11) 12. FQSYVDRFYKSLRAEQTD (SEQ ID NO: 12)
13. QNANPDCKLVLKGL (SEQ ID NO:13) 14. NPTL-EEMLTACQG (SEQ ID NO: 14)
15. GGPGQKARLMAEALKE (SEQ ID NO: 15) 16. ARQCRAPRRQGCWKCGK (SEQ ID NO: 16)

These peptides are prepared synthetically and, conveniently, are modified by chemical means. These peptides as well as shorter subpeptides thereof being up to 7 amino acids long are likewise part of the invention as are their modified forms. Furthermore, peptides from constant regions of other HIV-$2_{D205}$ genes are also part of the invention, provided the deviation from the consensus sequence is not more than 20%.

Likewise, the strongly deviating protein regions [such as rev (aa 2–11), vif (aa 186–202), env (aa 2–23; 118–204; etc.)] are regarded as being suitable for vaccine preparation, since they are believed to induce mechanisms causing natural (and successful) defense against HIV-$2_{D205}$.

The same regions as for vaccines also hold for geno- and immunotherapy. The constant regions are hoped to provide a spectrum of virus variants as broad as possible, which is covered by the therapeutic agents. The less constant regions might just cause those immune responses that keep the viruses stalled.

For differential diagnostics, peptides or nucleic acids are possible which differ from the prototype HIV-$2_{ROD}$ as strongly as possible. Besides the unique 54 bp insertion (see above) in the gag/pol overlap region, those are to be found especially in the genes rev and vif.

Due to close relationship to monkey viruses, and setting out from the principle that vaccines from precursor strains are able to develop a broader protection efficacy, HIV-$2_{D205}$ is particularly suitable for the preparation of vaccines protecting against HIV infections. This virus can be grown in a monkey as the suitable host, and the resulting antibodies may be used as a vaccine for human application. Thus, the vaccine protects against infection of a spectrum of virus variants as broad as possible.

Furthermore, it is possible to employ peptide assays or PCR assays on the basis of HIV-$^2$D$_{205}$ that enable to distinguish HIV-$^2$D$_{205}$ from other HIV.

The figures as well as the tables are described below:

Table 1 shows nucleotide sequence homology between HIV and SIV in percent. The sequences were compared using MICROGENIE™ sequence software of the company Beckman.

Table 2 shows sequence conservation of genetic elements of the nucleotide and amino acid region.

FIG. 1 shows the analysis of the deduced ORF-Y (open reading frame) amino acid sequence at positions 1851 to 1651 in the lower HIV-2$_{D205}$ sequence region. a) shows the amino acid orientation of the putative proteins of ORF-Y of different HIV-2 strands, SIV$_{sm}$ and SIV$_{mac}$.b) shows the profiles of the deduced ORF-Y proteins of HIV-2$_{D205}$ using the Beckman MICROGENIE ™ analyzing program.

FIG. 2 shows the amino acid sequence of the external glycoproteins of the HIV-2/SIV$_{sm}$/SIV$_{mac}$ group viruses. The sequenced clone HIV-2$_{D205}$ contained only 75% of the external glycoprotein. The potential N-glycosylation sites are underlined. The conserved cysteine sites are marked with an asterisk.

In FIG. 3, the size of the external glyco-proteins of HIV-2$_{ROD}$ is compared to that of HIV-2$_{D205}$. Cell proteins enriched with $^{35}$S--cysteine were infected with HIV--2$_{ROD}$ (columns 1 and 2) and HIV-2$_{D205}$ (columns 3 and 4), immunoprecipitated with HIV-2-positive serum and separated using an 8,5% SDS polyacrylic amide gel. The external glycoprotein of HIV-2$_{ROD}$ (gp 125) and its precursor (gp 140), the dimeric form of gp 140 (gp 300) and the positions of molecular dimensions are given in daltons. With HIV-2$_{D205}$-infected cells, the band characterizing a dimer cannot be seen. Similarly, following treatment with castanospermine, column 4, an inhibitor of glucosidase 1, the dimeric form only occurs with HIV-$^2$ROD, column 2. Furthermore, it is remarkable that the external glycoprotein as well as its precursor are larger in size with HIV-$^2$D$_{205}$ than with HIV-2$_{ROD}$.

FIG. 4 shows the minimum length evolutionary tree indicating relationship of HIV-2$_{D205}$ with the other HIV/SIV--subtypes. The tree was set up by single base substitutions in the 3'-region of the HIV-2$_{D205}$ sequence using PAUP™ [Smith, T. F. et al., Nature 333, 573 –575 (1988)] and the PHYLIP™ bootstrapping algorithm Version 3.21.

FIG. 5 shows the amino acid sequences derived from single genes of the HIV-2$_{D205}$, 7 and HIV-2$_{ROD}$ sequence, respectively, and compared to the amino acid consensus sequences derived from all previously sequenced HIV-2 and SIV$_{mac}$/SIV$_{sm}$ sequences. Among the amino acids of HIV-2$_{D205}$, 7 (5$a$) and HIV-2$_{ROD}$ (5$b$), respectively, deviating from the consensus sequence, it was determined which percentage was identical to the HIV-2 consensus sequence (black bars), which was identical to the SIV$_{mac}$/SIV$_{sm}$ consensus sequence (grey bars), and which percentage corresponded to new amino acids (light bars).

We claim:

1. A preparation comprising a peptide selected from teh group consisting of ESCDKHYWD (SEQ ID NO:2), RFRYCAPPG (SEQ ID NO:3), LLRCNDTNYSGF (SEQ ID NO: 4), STWFGFNGTRAENRYIYWH (SEQ ID NO:5), DNRTIISLN (SEQ ID NO:6), NELDRFGLAESLLE (SEQ ID NO: 7), PLVPTGSENLKSL (SEQ ID NO: 8), PLSPRTLNAWVKL (SEQ ID NO: 9) EEKKFGAEVVPGFQALSEGCTPYEINQMLNCV (SEQ ID NO: 10), GLQKCVRMYNPTNILD (SEQ ID NO:11), FQSYVDRFYKSLRAEQTD (SEQ ID NO: 12), QNANPDCKLVLKGL (SEQ ID NO: 13), NPTLEEMLTACQG (SEQ ID NO: 14), GGPGQKARLMAEALKE (SEQ ID NO: 15), ARQCRAPRRQGCWKCGK (SEQ ID NO: 16), fragments thereof having a length of up to 7 amino acids, and mixtures thereof.

2. A method of detecting HIV or SIV comprising admixing the preparaton of claim 1 with a sample for differential diagnosis.

3. The method of claim 2, wherein diagnosis is by protein assay or PCR assay.

4. A peptide preparation comprising a peptide selected from the group consisting of ESCDKHYWD (SEQ ID NO: 2), RFRYCAPPG (SEQ ID NO: 3), LLRCNDTNYSGF (SEQ ID NO: 4), STWFGFNGTRAENRYIYWH (SEQ ID NO: 5), DNRTIISLN (SEQ ID NO: 6), NELDRFGLAESLLE (SEQ ID NO: 7), PLVPTGSENLKSL (SEQ ID NO: 8), PLSPRTLNAWVKL (SEQ ID NO: 9), EEKKF- GAEVVPGFQALSEGCTPYEINQMLNCV (SEQ ID NO: 10), GLQKCVRMYNPTNILD (SEQ ID NO: 11), FQSYVDRFYKSLRAEQTD (SEQ ID NO: 12), QNANPDCKLVLKGL (SEQ ID NO: 13), NPTLEEMLTACQG (SEQ ID NO: 14), GGPGQKARLMAEALKE (SEQ ID NO: 15), ARQCRAPRRQGCWKCGK (SEQ ID NO: 16), and mixtures thereof.

5. A preparation according to claim 4, which further comprises from HIV-$2_{D205}$ amino acid sequence 2–11 of rev, amino acid sequence 186–200 of vif, amino acid sequence 2–33 of env, amino acid sequence 118–204 of env, or a mixture thereof.

6. A peptide selected from the group consisting of ESCDKHYWD (SEQ ID NO:2), RFRYCAPPG (SEQ ID NO: 3), LLRCNDTNYSGF (SEQ ID NO: 4), STWFGFNGTRAENRYIYWH (SEQ ID NO: 5), DNRTIISLN (SEQ ID NO: 6), NELDRFGLAESLLE (SEQ ID NO: 7), PLVPTGSENLKSL (SEQ ID NO: 8), PLSPRTLNAWVKL (SEQ ID NO: 9), EEKKFGAEVVPGFQALSEGCTPYEINQMLNCV (SEQ ID NO: 10), GLQKCVRMYNPTNILD (SEQ ID NO: 11), FQSYVDRFYKSLRAEQTD (SEQ ID NO: 12), QNANPDCKLVLKGL (SEQ ID NO: 13), NPTLEEMLTACQG (SEQ ID NO: 14), GGPGQKARLMAEALKE (SEQ ID NO: 15), ARQCRAPRRQGCWKCGK (SEQ ID NO: 16), or a fragment, thereof, having a length of up to 7 amino acids, and mixtures thereof.

7. The peptide of claim 6 that is, ESCDKHYWD (SEQ ID NO: 2).

8. The peptide of claim 6 that is RFRYCAPPG (SEQ ID NO: 3).

9. The peptide of claim 6 that is LLRCNDTNYSGF (SEQ ID NO: 4).

10. The peptide of claim 6 that is STWFGFNGTRAENRYIYWH (SEQ ID NO: 5).

11. The peptide of claim 6 that is DNRTIISLN (SEQ ID NO: 6).

12. The peptide of claim 6 that is NELDRFGLAESLLE (SEQ ID NO: 7).

13. The peptide of claim 6 that is PLVPTGSENLKSL (SEQ ID NO: 8).

14. The peptide of claim 6 that is PLSPRTLNAWVKL (SEQ ID NO: 9).

15. The peptide of claim 6 that is EEKKFGAEVVPGFQALSEGCTPYEINQ-MLNCV (SEQ ID NO: 10).

16. The peptide of claim 6 that is GLQKCVRMYNPTNILD (SEQ ID NO: 11).

17. The peptide of claim 6 that is FQSYVDRFYKSLRAEQTD (SEQ ID NO: 12).

18. The peptide of claim 6 that is QNANPDCKLVLKGL (SEQ ID NO: 13).

19. A method of using the peptide of claim 6 for producing antibodies to HIV-$2_{D205}$ in vitro.

* * * * *

UNITED STATES PATENT AND TRADEMARK OFFICE
CERTIFICATE OF CORRECTION

PATENT NO.   : 5,861,243
DATED        : January 19, 1999
INVENTOR(S)  : Ursula Dietrich et al.

It is certified that error appears in the above-identified patent and that said Letters Patent is hereby corrected as shown below:

Title page,
Item [54], after "AND" delete "AGENT";

Column 1,
Line 4, after "AND" delete "AGENT".

Column 2,
Line 41, delete "HIV-$^2$D$_{205}$" and insert -- HIV-$2_{D205}$ --.

Column 3,
Line 33, delete "ana-lyses" and insert -- analyses --;
Line 49, delete "HIV-$2_{D05}$" and insert -- HIV-$2_{D205}$ --.

Column 4,
Line 55, delete "po0" and insert -- pol --.

Column 5,
Line 37, delete "SIV$_{max}$" and insert -- SIV$_{mac}$ --.

Column 7,
Line 2, delete "HIV-$^2$D$_{205}$" and insert -- HIV-$2_{D205}$ --; and
Line 3, delete "HIV-$^2$D$_{205}$" and insert -- HIV-$2_{D205}$ --;

Column 8,
Line 8, delete "HIV-$^2$ROD" and insert -- HIV-$2_{ROD}$ --;
Line 10, delete "HIV-$^2$D$_{205}$" and insert -- HIV-$2_{D205}$ --;

UNITED STATES PATENT AND TRADEMARK OFFICE
CERTIFICATE OF CORRECTION

PATENT NO. : 5,861,243
DATED : January 19, 1999
INVENTOR(S) : Ursula Dietrich et al.

It is certified that error appears in the above-identified patent and that said Letters Patent is hereby corrected as shown below:

Column 15,
Line 55, delete "teh" and insert -- the --.

Column 16,
Line 57, delete "preparation" and insert -- preparation --.

Column 18,
Line 25, delete "peptide" and insert -- peptides --.

Signed and Sealed this

Eleventh Day of December, 2001

*Attest:*

NICHOLAS P. GODICI
*Attesting Officer*     *Acting Director of the United States Patent and Trademark Office*

UNITED STATES PATENT AND TRADEMARK OFFICE
CERTIFICATE OF CORRECTION

PATENT NO.      : 5,861,243
DATED           : June 19, 1999
INVENTOR(S)     : Ursula Dietrich et al.

Page 1 of 2

It is certified that error appears in the above-identified patent and that said Letters Patent is hereby corrected as shown below:

Column 8,
Between line 28 and sequence listing, insert:

TABLE 1   Nucleotide sequence homology between HIVs and SIVs (in %)

| STRAIN | HIV-2 | | | | SIV | | | HIV-1 |
|---|---|---|---|---|---|---|---|---|
|  | ROD | D194 | HTH2 | TSY | SM | MAC | AGM | BRU |
| HIV-2ben r | 76.8 | 76.2 | 76.4 | 76.7 | 76.4 | 75.0 | 58.2 | 57.8 |
| HIV-2r+b | -- | 87.0 | 90.1 | 89.3 | 77.7 | 76.3 | 58.0 | 57.0 |
| SIVmac251 | 76.3 | 75.3 | 76.4 | 75.8 | 84.6 | -- | 58.7 | 55.0 |

UNITED STATES PATENT AND TRADEMARK OFFICE
CERTIFICATE OF CORRECTION

PATENT NO.    : 5,861,243
DATED         : June 19, 1999
INVENTOR(S)   : Ursula Dietrich et al.

It is certified that error appears in the above-identified patent and that said Letters Patent is hereby corrected as shown below:

<u>Column 8, cont'd.</u>

TABLE 2

Sequence conservation of genetic elements (nucleotide/amino acid level)

| $HIV-2_{D205}$ genetic element | % homology to $HIV-2_{ROD}$ | $SIV_{SM}$ | $SIV_{MAC251}$ |
|---|---|---|---|
| U3 | 72.9 | 66.8 | 63.5 |
| R | 95.4 | 94.3 | 91.6 |
| U5 | 88.9 | 87.2 | 87.1 |
| gag | 81.5/84.5 | 82.5/87.2 | 80.6/83.7 |
| pol | 79.0/82.0 | 84.7/82.4 | 77.4/77.1 |
| vif | 72.4/68.9 | 72.9/68.7 | 72.0/61.0 |
| vpx | 76.1/75.2 | 76.4/75.2 | 75.2/77.9 |
| vpr | 78.8/69.8 | 74.8/73.4 | 78.9/76.4 |
| tat ex1 | 78.4/66.3 | 76.0/60.5 | 81.1/66.3 |
| rev ex1 | 67.1/56.5 | 64.1/52.4 | 70.0/60.9 |
| env (partial) | 70.0/67.0 | 68.8/65.6 | 68.6/65.7 |
| nef (partial) | 73.5/72.1 | 66.5/62.8 | 66.6/58.3 |

Signed and Sealed this

First Day of October, 2002

Attest:

Attesting Officer

JAMES E. ROGAN
Director of the United States Patent and Trademark Office

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: Human immunodeficiency virus type 2
        ( B ) STRAIN: D205

( x i ) SEQUENCE DESCRIPTION: SEQ ID NO:1:

Leu  Phe  Glu  Thr  Ser  Ile  Lys  Pro  Cys  Val  Lys  Leu
    1                      5                              10

( 2 ) INFORMATION FOR SEQ ID NO:2:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Human immunodeficiency virus type 2
        ( B ) STRAIN: D205

( x i ) SEQUENCE DESCRIPTION: SEQ ID NO:2:

Glu  Ser  Cys  Asp  Lys  His  Tyr  Trp  Asp (2) INFORMATION FOR SEQ ID NO:3:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (vi) ORIGINAL SOURCE:
        (A) ORGANISM: Human immunodeficiency virus type 2
        (B) STRAIN: D205

(xi) SEQUENCE DESCRIPTION: SEQ ID NO:3:

```
Arg Phe Arg Tyr Cys Ala Pro Pro Gly
1               5
```

(2) INFORMATION FOR SEQ ID NO:4:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (vi) ORIGINAL SOURCE:
        (A) ORGANISM: Human immunodeficiency virus type 2
        (B) STRAIN: D205

(xi) SEQUENCE DESCRIPTION: SEQ ID NO:4:

```
Leu Leu Arg Cys Asn Asp Thr Asn Tyr Ser Gly Phe
1               5                   10
```

(2) INFORMATION FOR SEQ ID NO:5:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (vi) ORIGINAL SOURCE:
        (A) ORGANISM: Human immunodeficiency virus type 2
        (B) STRAIN: D205

(xi) SEQUENCE DESCRIPTION: SEQ ID NO:5:

```
Ser Thr Trp Phe Gly Phe Asn Gly Thr Arg Ala Glu Asn Arg Tyr
1               5                   10                  15

Ile Tyr Trp His
```

(2) INFORMATION FOR SEQ ID NO:6:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (vi) ORIGINAL SOURCE:
        (A) ORGANISM: Human immunodeficiency virus type 2
        (B) STRAIN: D205

(xi) SEQUENCE DESCRIPTION: SEQ ID NO:6:

```
Asp Asn Arg Thr Ile Ile Ser Leu Asn
1               5
```

( 2 ) INFORMATION FOR SEQ ID NO:7:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Human immunodeficiency virus type 2
        ( B ) STRAIN: D205

( x i ) SEQUENCE DESCRIPTION: SEQ ID NO:7:

```
Asn Glu Leu Asp Arg Phe Gly Leu Ala Glu Ser Leu Leu Glu
1               5                   10
```

( 2 ) INFORMATION FOR SEQ ID NO:8:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Human immunodeficiency virus type 2
        ( B ) STRAIN: D205

( x i ) SEQUENCE DESCRIPTION: SEQ ID NO:8:

```
Pro Leu Val Pro Thr Gly Ser Glu Asn Leu Lys Ser Leu
1               5                   10
```

( 2 ) INFORMATION FOR SEQ ID NO:9:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Human immunodeficiency virus type 2
        ( B ) STRAIN: D205

( x i ) SEQUENCE DESCRIPTION: SEQ ID NO:9:

```
Pro Leu Ser Pro Arg Thr Leu Asn Ala Trp Val Lys Leu
1               5                   10
```

( 2 ) INFORMATION FOR SEQ ID NO:10:

( i ) SEQUENCE CHARACTERISTICS:
        ( A ) LENGTH: 32 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Human immunodeficiency virus type 2
        ( B ) STRAIN: D205

( x i ) SEQUENCE DESCRIPTION: SEQ ID NO:10:

```
Glu Glu Lys Lys Phe Gly Ala Glu Val Val Pro Gly Phe Gln Ala
1               5                   10                  15
Leu Ser Glu Gly Cys Thr Pro Tyr Glu Ile Asn Gln Met Leu Asn
                20                  25                  30
Cys Val
```

( 2 ) INFORMATION FOR SEQ ID NO:11:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Human immunodeficiency virus type 2
        ( B ) STRAIN: D205

( x i ) SEQUENCE DESCRIPTION: SEQ ID NO:11:

```
Gly Leu Gln Lys Cys Val Arg Met Tyr Asn Pro Thr Asn Ile Leu
1               5                   10                  15
Asp
```

( 2 ) INFORMATION FOR SEQ ID NO:12:

( i ) SEQUENCE CHARACTERISTICS:
        ( A ) LENGTH: 18 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Human immunodeficiency virus type 2
        ( B ) STRAIN: D205

( x i ) SEQUENCE DESCRIPTION: SEQ ID NO:12:

```
Phe Gln Ser Tyr Val Asp Arg Phe Tyr Lys Ser Leu Arg Ala Glu
1               5                   10                  15
Gln Thr Asp
```

( 2 ) INFORMATION FOR SEQ ID NO:13:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Human immunodeficiency virus type 2
        ( B ) STRAIN: D205

( x i ) SEQUENCE DESCRIPTION: SEQ ID NO:13:

```
Gln Asn Ala Asn Pro Asp Cys Lys Leu Val Leu Lys Gly Leu
1               5                   10
```

( 2 ) INFORMATION FOR SEQ ID NO:14:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Human immunodeficiency virus type 2
        ( B ) STRAIN: D205

( x i ) SEQUENCE DESCRIPTION: SEQ ID NO:14:

```
Asn Pro Thr Leu Glu Glu Met Leu Thr Ala Cys Gln Gly
1               5                   10
```

(2) INFORMATION FOR SEQ ID NO:15:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (vi) ORIGINAL SOURCE:
        (A) ORGANISM: Human immunodeficiency virus type 2
        (B) STRAIN: D205

(xi) SEQUENCE DESCRIPTION: SEQ ID NO:15:

```
Gly Gly Pro Gly Gln Lys Ala Arg Leu Met Ala Glu Ala Leu Lys
1               5                   10                  15
Glu
```

(2) INFORMATION FOR SEQ ID NO:16:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (vi) ORIGINAL SOURCE:
        (A) ORGANISM: Human immunodeficiency virus type 2
        (B) STRAIN: D205

(xi) SEQUENCE DESCRIPTION: SEQ ID NO:16:

```
Ala Arg Gln Cys Arg Ala Pro Arg Arg Gln Gly Cys Trp Lys Cys
1               5                   10                  15
Gly Lys
```

(2) INFORMATION FOR SEQ ID NO:17:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Human immunodeficiency virus type 2
        (B) STRAIN: D205

(xi) SEQUENCE DESCRIPTION: SEQ ID NO:17:

```
AACCCAGCAG AGGGCATGAC ACCTCGGGGG GCGACACCAT CTGCGCCCCC TGCA        54
```